(12) United States Patent
Mackool (10) Patent No.: US 10,639,195 B1
(45) Date of Patent: May 5, 2020

(54) CAPSULAR RETRACTORS

(71) Applicant: Richard Mackool, Sarasota, FL (US)

(72) Inventor: Richard Mackool, Sarasota, FL (US)

(*) Notice: Subject to any disclaimer, the term of this patent is extended or adjusted under 35 U.S.C. 154(b) by 0 days.

(21) Appl. No.: 16/544,300

(22) Filed: Aug. 19, 2019

(51) Int. Cl.
 *A61F 9/007* (2006.01)
 *A61F 2/16* (2006.01)
 *A61F 9/00* (2006.01)

(52) U.S. Cl.
 CPC .......... *A61F 9/007* (2013.01); *A61F 2/16* (2013.01); *A61F 9/0017* (2013.01); *A61L 2430/16* (2013.01)

(58) Field of Classification Search
 CPC ........ A61B 17/2841; A61B 17/2909; A61B 2017/0042; A61B 2017/00424; A61B 2017/00429; A61B 2017/00433; A61B 2017/00438; A61B 2017/00442; A61B 2017/00446; A61B 2017/00451; A61B 2017/00455; A61B 2017/0046; A61B 2017/00464; A61B 2017/00469; A61B 2017/00473; A61B 2017/291; A61B 2017/2911; A61B 2017/2918; A61F 9/007; A61F 9/0017; A61F 9/00709; A61F 9/00727; A61F 9/00736; A61F 9/00745; A61F 9/00754; A61F 2002/9517; A61F 2/16; A61L 2430/16
 See application file for complete search history.

(56) References Cited

U.S. PATENT DOCUMENTS

| | | | |
|---|---|---|---|
| 3,955,578 A | 5/1976 | Chamness | |
| 4,538,611 A | 9/1985 | Kelman | |
| 4,732,150 A | 3/1988 | Keener, Jr. | |
| 4,766,897 A | 8/1988 | Smirmaul | |
| 4,844,065 A | 7/1989 | Faulkner | |
| 4,869,716 A | 9/1989 | Smirmaul | |
| 4,950,272 A | 8/1990 | Smirmaul | |
| 4,960,418 A | 10/1990 | Tennant | |
| 5,098,439 A | 3/1992 | Hill et al. | |
| 5,171,314 A | 12/1992 | Dulebohn | |
| 5,201,741 A | 4/1993 | Dulebohn | |
| 5,445,637 A | 8/1995 | Bretton | |
| 6,517,550 B1 | 2/2003 | Konya | |
| 6,551,326 B1 | 4/2003 | Van Heugten | |
| 6,743,228 B2 | 6/2004 | Lee et al. | |
| 8,118,862 B2 | 2/2012 | Saeed | |

(Continued)

OTHER PUBLICATIONS

You Tube Video "Phaco Section by Wire Snare, by Dr. Samar K. Basak—Dlsha Eye Hospitals" Published on Jan. 30, 2013; internet address:<https://youtu.be/CP8jrVb8qrg>.

(Continued)

*Primary Examiner* — Tan-Uyen T Ho
*Assistant Examiner* — Chima U Igboko
(74) *Attorney, Agent, or Firm* — Carter, DeLuca & Farrell LLP (57) ABSTRACT

A capsular retractor includes an elongated shaft, a hook portion extending from a distal end portion of the elongated shaft, a handle portion extending from a proximal end portion of the elongated shaft, and first and second grasping segments formed with or attached to the handle portion. The grasping segments are configured to be selectively grasped for manipulating the ophthalmic surgical instrument regardless of the rotational orientation of the handle portion.

20 Claims, 4 Drawing Sheets

(56) References Cited

U.S. PATENT DOCUMENTS

| | | |
|---|---|---|
| 8,252,019 B2 | 8/2012 | Fleming, III |
| 8,814,854 B2 | 8/2014 | Jia |
| 8,821,567 B2 | 9/2014 | Saeed |
| 9,039,713 B2 | 5/2015 | Segermark |
| 9,629,747 B2 | 4/2017 | Clauson et al. |
| 9,775,743 B2 | 10/2017 | Clauson et al. |
| 10,292,862 B1 | 5/2019 | Mackool |
| 2004/0092953 A1 | 5/2004 | Salameh |
| 2004/0092982 A1 | 5/2004 | Sheffer |
| 2009/0054904 A1 | 2/2009 | Holmen |
| 2009/0082787 A1 | 3/2009 | Pang |
| 2009/0216260 A1* | 8/2009 | Souza ............ A61B 17/3417 606/185 |
| 2010/0312252 A1 | 12/2010 | Jia et al. |
| 2013/0197533 A1* | 8/2013 | Dusek ............ A61F 9/00736 606/107 |
| 2014/0364885 A1 | 12/2014 | Wells |
| 2015/0257927 A1 | 9/2015 | Olson |
| 2016/0074220 A1 | 3/2016 | Ianchulev et al. |
| 2016/0143778 A1 | 5/2016 | Aljuri |
| 2016/0346121 A1 | 12/2016 | Ianchulev |
| 2017/0312125 A1 | 11/2017 | Clauson et al. |
| 2018/0036170 A1 | 2/2018 | Ghannoum et al. |
| 2018/0036171 A1 | 2/2018 | Clauson et al. |
| 2018/0064578 A1 | 3/2018 | Clauson |
| 2018/0318132 A1 | 11/2018 | Clauson |
| 2018/0318133 A1 | 11/2018 | Clauson |

OTHER PUBLICATIONS

Bhattacharya, "Nuclear management in manual small incision cataract surgery by snare technique", Indian J. Ophthalmology, Feb. 2009, vol. 57, No. 1; 11 pages.

International Search Report dated Jul. 12, 2019, issued in International Appln. No. PCT/US19/29588.

* cited by examiner

CAPSULAR RETRACTORS

BACKGROUND

Technical Field

The present disclosure relates to instruments used in eye surgery, and more particularly, to ophthalmic surgical instruments that stabilize a lens capsule during or after cataract surgery.

Background of Related Art

Cataract surgery and other surgical procedures that treat lenticular tissue, such as, for example, the intraocular lens, are performed by making a small incision in the edge of the cornea, which provides access to the anterior chamber and to the anterior surface of the lens capsule. Afterward, a generally circular incision called a capsulorhexis is made through the anterior surface of the lens capsule to provide surgical access to the lens. The cataractous nucleus and cortex of the natural lens is removed from the capsular bag and an artificial lens implant is inserted into the bag through the capsulorhexis. During removal of the lens or implantation of a new lens, it is desirable to stabilize the lens capsule and/or retract the lens capsule.

SUMMARY

In accordance with an aspect of the present disclosure, an ophthalmic surgical instrument for stabilizing a lens capsule is provided and includes an elongated shaft having a proximal end portion and a distal end portion, a hook portion extending from the distal end portion of the elongated shaft, a handle portion extending from the proximal end portion of the elongated shaft, a first arm extending laterally from the handle portion, and a second arm extending laterally from the handle portion and longitudinally spaced along the elongated shaft from the first arm. The first and second arms are oriented at a non-parallel angle relative to one another and are configured to be selectively grasped for manipulating the ophthalmic surgical instrument.

In aspects, the angle between the first and second arms may be from about 10 degrees to about 90 degrees.

In aspects, the first and second arms may be perpendicular to one another and a longitudinal axis defined by the handle portion.

In aspects, the first arm may have a first end portion projecting from a first side of the handle portion, and a second end portion projecting from a second side of the handle portion.

In aspects, the second arm may have a first end portion projecting from a third side of the handle portion, and a second end portion projecting from a fourth side of the handle portion.

In aspects, the first and second sides of the handle portion may oppose one another, and the third and fourth sides of the handle portion may oppose one another.

In aspects, the hook portion may extend at an acute angle relative to a longitudinal axis defined by the elongated shaft.

In aspects, the handle portion may extend at an obtuse angle relative to the longitudinal axis of the elongated shaft.

In aspects, the elongated shaft may define a first longitudinally-extending plane and a second longitudinally-extending plane. The first and second planes are perpendicular to one another. The hook portion and the handle portion may be coplanar with the first plane, and the hook portion and the handle portion may be disposed on opposite sides of the second plane.

In aspects, each of the first and second arms may have a flat, rectangular configuration.

In aspects, the ophthalmic surgical instrument may further include a stopper disposed about the handle portion at a location distally of the first and second arms.

In accordance with another aspect of the present disclosure, an ophthalmic surgical instrument for stabilizing a lens capsule is provided that includes an elongated shaft, a hook portion, and a handle assembly. The elongated shaft defines a longitudinal axis and has a proximal end portion and a distal end portion. The hook portion extends at an acute angle relative to the distal end portion of the elongated shaft. The handle assembly is attached to the proximal end portion of the elongated shaft and includes an elongated handle portion, a first arm extending outwardly from opposite first and second sides of the elongated handle portion, and a second arm extending outwardly from opposite third and fourth sides of the elongated handle portion. The first and second arms are configured to be selectively grasped for manipulating the ophthalmic surgical instrument.

In aspects, the first and second arms may be oriented at a non-parallel angle relative to one another.

In accordance with yet another aspect of the present disclosure, a capsular retractor is provided and includes an elongated shaft having a proximal end portion and a distal end portion, a hook portion extending from the distal end portion of the elongated shaft, and an elongated handle portion attached to the distal end portion of the elongated shaft. The elongated handle portion includes a first grasping segment and a second grasping segment disposed perpendicular to the first grasping segment. The first and second grasping segments are configured to be selectively grasped for manipulating the ophthalmic surgical instrument.

In aspects, the second grasping segment may be disposed distally of the first grasping segment.

In aspects, each of the first and second grasping segments may be flat and define a plane. The plane of the first grasping segment may be perpendicular to the plane of the second grasping segment.

In accordance with yet another aspect of the present disclosure, a capsular retractor is provided and includes an elongated shaft having a proximal end portion and a distal end portion, a hook portion extending from the distal end portion of the elongated shaft, an elongated handle portion attached to the distal end portion of the elongated shaft, and first and second arms extending transversely through the elongated handle portion. The first arm is set at a first radial position around the handle portion, and the second arm is set at a second radial position around the handle portion. The first and second radial positions are different from one another. The first and second arms are configured to be selectively grasped for manipulating the ophthalmic surgical instrument.

In aspects, the second arm may be disposed distally of the first arm.

In aspects, the first and second radial positions may be from about 10 degrees to about 90 degrees relative to one another.

In accordance with yet another aspect of the present disclosure, a method of using an ophthalmic surgical instrument is provided. The method includes positioning a hook portion of the ophthalmic surgical instrument around an inner peripheral edge of a capsular bag; grasping a first arm of a handle portion of the ophthalmic surgical instrument;

and manipulating the ophthalmic surgical instrument using the first arm. The handle portion has a second arm offset from the first arm.

In aspects, the ophthalmic surgical instrument may be manipulated before, during, or after positioning the hook portion around the inner peripheral edge of the capsular bag.

In aspects, the method may further include grasping the second arm of the handle portion; and manipulating the ophthalmic surgical instrument using the second arm.

As used herein, the terms parallel and perpendicular are understood to include relative configurations that are substantially parallel and substantially perpendicular up to about + or −25 degrees from true parallel and true perpendicular.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

BRIEF DESCRIPTION OF THE DRAWINGS

Embodiments of the present disclosure are described herein with reference to the accompanying drawings, wherein.

DETAILED DESCRIPTION

Embodiments of the presently disclosed ophthalmic surgical instruments are described in detail with reference to the drawings, in which like reference numerals designate identical or corresponding elements in each of the several views. As used herein and as is traditional, the term "distal" will refer to that portion of the ophthalmic surgical instrument which is further from the user (i.e., closer to the eye) while the term "proximal" will refer to that portion of the ophthalmic surgical instrument which is closer to the user (i.e., further from the eye).

The present disclosure provides a hand-held ophthalmic surgical instrument for stabilizing a lens capsule in a patient's eye during or after an ophthalmic surgical procedure, such as, for example, cataract surgery. The ophthalmic surgical instrument includes a handle portion, a shaft extending distally from the handle portion, and a hooked distal end attached to the shaft. The handle portion has a pair of appendages extending laterally from the handle portion for grasping with a forceps or by a clinician's fingers. The appendages are spaced longitudinally from one another along the handle portion and are angled relative to one another to facilitate manipulation of the ophthalmic surgical instrument regardless of the rotational orientation of the ophthalmic surgical instrument. These and other features and advantages of the various embodiments of the disclosed ophthalmic surgical instruments will be described below.

Figure 1:
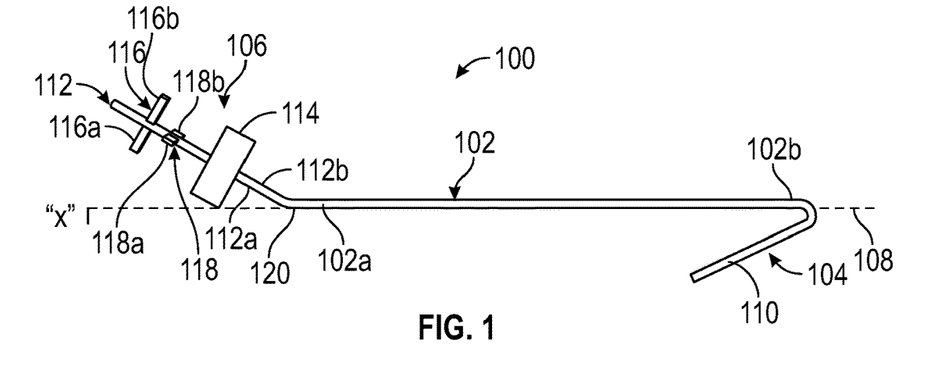
FIG. 1 is a side perspective view of an ophthalmic surgical instrument in accordance with an embodiment of the present disclosure.
Figure 2:
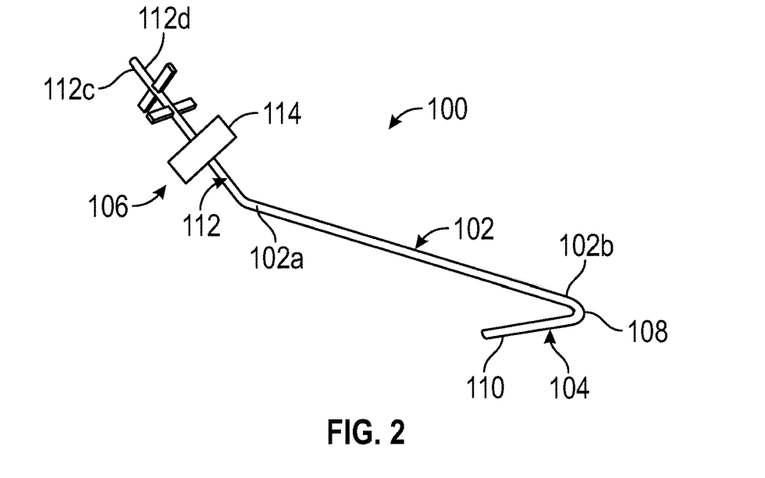
FIG. 2 is a perspective view of the ophthalmic surgical instrument of FIG. 1.

With reference to FIGS. 1 and 2, an exemplary embodiment of an ophthalmic surgical instrument, such as, for example, a capsular retractor, is illustrated and is generally designated 100. The ophthalmic surgical instrument 100 generally includes an elongated shaft 102, a hook portion 104 attached to a distal end portion 102b of the elongated shaft 102, and a handle assembly 106 attached to a proximal end portion 102a of the elongated shaft 102. The elongated shaft 102, the handle assembly 106, and the hook portion 104 may be monolithically formed with one another from any suitable type of material or may be connected to one another via various fastening engagements, such as, for example, adhesive, welds, rivets, or the like. The ophthalmic surgical instrument 100 may be fabricated from a metal, such as stainless steel, a plastic, such as a thermoplastic, or any other suitable material that maintains structural rigidity during use. The elongated shaft 102 defines a longitudinal axis "X" and has a length sufficient to extend from the capsular bag "C" (FIG. 3) of a patient's eye "E" and out of a cornea "K." In aspects, the elongated shaft 102 may be linear along its length or assume a curved or angular profile. The elongated shaft 102 may be flattened along its length, such that the elongated shaft 102 assumes a flat, rectangular transverse cross-sectional shape.

The hook portion 104 includes a bent portion 108 extending from the distal end portion 102b of the elongated shaft 102, and a shank 110 extending from the bent portion 108. The bent portion 108 is such that the shank 110 extends relative to the longitudinal axis "X" of the elongated shaft "X" at an acute angle, such as, for example, from about 0 degrees (e.g., parallel) to about 60 degrees. In some aspects, the acute angle between the shank 110 and the elongated shaft 102 may be from about 0 degrees to about 45 degrees. The shank 110 is illustrated as having a linear configuration, but other shapes for the shank 110 are contemplated such as curved or angular. The length of the shank 110 may be from about 1.6 mm to about 5.0 mm and, in some aspects, from about 2.0 mm to about 3.0 mm.

The handle assembly 106 is coupled to the proximal end portion 102a of the elongated shaft 102 and includes an elongated handle portion 112, a stopper 114 disposed about the elongated handle portion 112, and first and second arms 116, 118 attached to the elongated handle portion 112. The elongated handle portion 112 may assume a linear configuration and have a flattened or plate-like configuration to facilitate grasping by a forceps. The elongated handle portion 112 may have a length of about half of the length of the elongated shaft 102. However, it is contemplated that the elongated handle portion 112 may have any suitable length and shape. The elongated handle portion 112 may have a bent portion 120, such that the elongated handle portion 112 extends at an obtuse angle from the longitudinal axis "X" of the elongated shaft 102, such as, for example, from about 90 degrees (perpendicular) to about 180 degrees (coaxial).

The elongated handle portion 102 and the hook portion 104 are bent in opposite directions from the elongated shaft 102. In this way, the elongated handle portion 112 and the hook portion 104 are disposed on opposite sides of a first longitudinally-extending plane defined by the elongated shaft 102. The elongated handle portion 112, the elongated shaft 102, and the hook portion 104 may be coplanar along a second longitudinally-extending plane that is perpendicular to the first plane.

The stopper 114 of the handle assembly 106 is fabricated from rubber and has a disc shape. In aspects, the stopper 114 may be fabricated from any suitable material, such as plastics or metals, and may assume any suitable shape, such as toroidal, square, elongated, or the like. In aspects, the stopper 114 may have a flattened or plate-like configuration to facilitate grasping by a forceps. The stopper 114 is slidably disposed on the elongated handle portion 112 and movable therealong between a plurality of discrete positions due to the frictional engagement between the stopper 114 and the elongated handle portion 112. In aspects, the stopper 114 may be axially fixed to the elongated handle portion 112.

The first arm 116 of the handle assembly 106 is monolithically formed with or connected to a first location of the handle portion 112, and the second arm 118 of the handle assembly 106 is monolithically formed with or connected to a second location of the handle portion 112. The second location of the handle portion 112 is distal the first location, such that the first and second arms 116, 118 are longitudinally spaced from one another along the handle portion 112 while being disposed proximally of the stopper 114. The first and second arms 116, 118 are flat and have a generally rectangular configuration. In other aspects, the first and second arms 116, 118 may be plate-like, cylindrical, or assume any suitable shape.

The first arm 116 is set at a first radial position about the handle portion 112 and extends outwardly from the handle portion 112. In aspects, the first arm 116 may extend at any suitable angle relative to the handle portion 112, such as from about 10 degrees to about 90 degrees, and in some aspects, from about 45 degrees to about 90 degrees. The first arm 116 may be linear along its length or assume a curved or angular configuration. The first arm 116 has a first end portion 116a projecting from a first side 112a of the handle portion 112, and a second end portion 116b extending from a second side 112b of the handle portion 112, opposite the first side 112a. In aspects, the first and second end portions 116a, 116b are monolithically formed with one another and extend transversely through the handle portion 112. The first and second end portions 116a, 116b may be coaxial or extend at angles relative to one another, such as acute or obtuse.

The second arm 118 is set at a second radial position about the handle portion 112 and extends outwardly from the handle portion 112. The second radial position of the second arm 118 may be about 90 degrees relative to the first radial position of the first arm 116. In aspects, the second arm may extend at any suitable angle relative to the handle portion 112, such as from about 10 degrees to about 90 degrees, and in some aspects, from about 45 degrees to about 90 degrees. The second arm 118 may be linear along its length or assume a curved or angular configuration. The second arm 118 has a first end portion 118a projecting from a third side 112c of the handle portion 112, and a second end portion 118b extending from a fourth side 112d of the handle portion 112, opposite the third side 112c. In this way, upon viewing the handle assembly 106 in line with a longitudinal axis of the handle portion 112, the first and second arms 116, 118 are perpendicular to one another and the longitudinal axis of the handle portion 112. It is contemplated that the handle assembly 106 may include more than two arms, such as three or more arms each oriented at a different radial position relative to the longitudinal axis of the handle portion 112.

Figure 3:
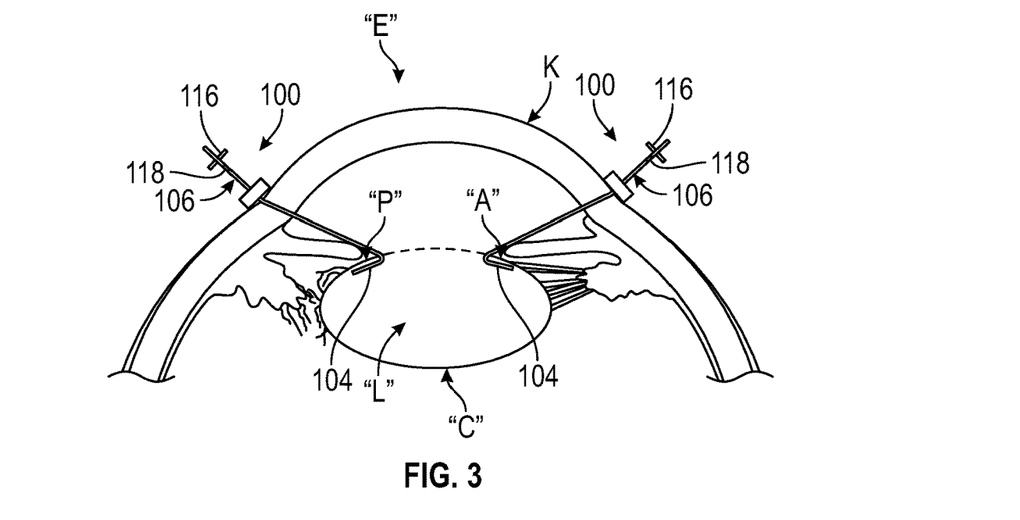
FIG. 3 is a sectional view illustrating a patient's eye being operated on by two of the ophthalmic surgical instruments of FIG. 1.

In operation, with reference to FIG. 3, one or a plurality of the ophthalmic surgical instruments 100 may be used to assist in an ophthalmic surgical procedure, such as, for example, a cataract surgery. During removal of a cataractous lens "L" from a lens capsule "C" (i.e., capsular bag) of a patient's eye "E" or during implantation of a replacement lens into the lens capsule "C," the ophthalmic surgical instruments 100 may be intraocularly positioned with the hook portions 104 around an inner peripheral edge "P" of the lens capsule "C" and under an underside of the lens capsule "C" with the handle assembly 106 disposed outside of the eye "E." An application of an outwardly-directed (e.g., generally proximally) force may be applied to the ophthalmic surgical instruments 100 to retract or maintain the position of the inner peripheral edge "P" of the lens capsule "C."

To properly orient the hook portion 104 relative to the lens capsule "C," the clinician may grasp one or both of the first and second arms 116, 118 with a forceps or with his or her pointer finger and thumb and apply a rotational force on the handle assembly 106 to adjust the rotational position of the hook portion 104. For example, in a situation where the first arm 116 is more readily grasped by the clinician due to its position relative to the eye "E" or the clinician, the first and second end portions 116a, 116b of the first arm 116 may be grasped with the forceps, whereby the clinician can easily manipulate the ophthalmic surgical instrument 100. In another situation where the second arm 118 may be more readily grasped by the clinician due to its position relative to the eye "E" or the clinician, the first and second end portions 118a, 118b of the second arm 118 may be grasped with the forceps, whereby the clinician can easily manipulate the ophthalmic surgical instrument 100.

Figure 4:
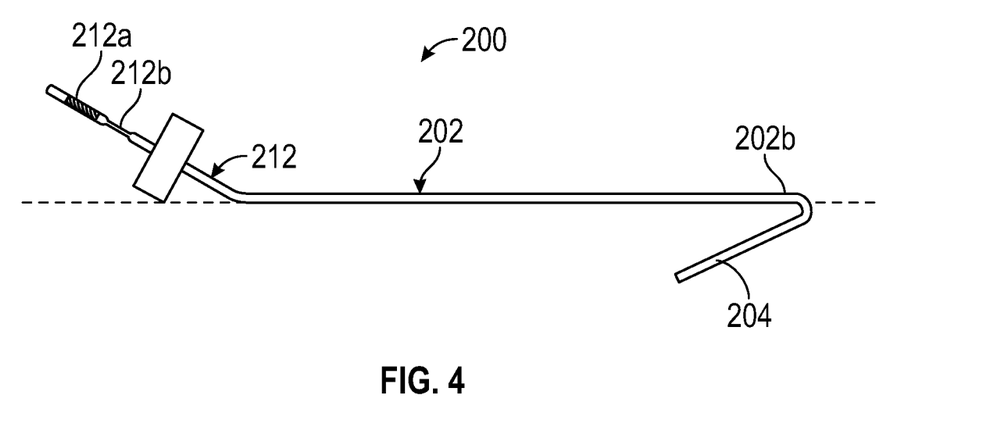
FIG. 4 is a side view of another embodiment of an ophthalmic surgical instrument.
Figure 5:
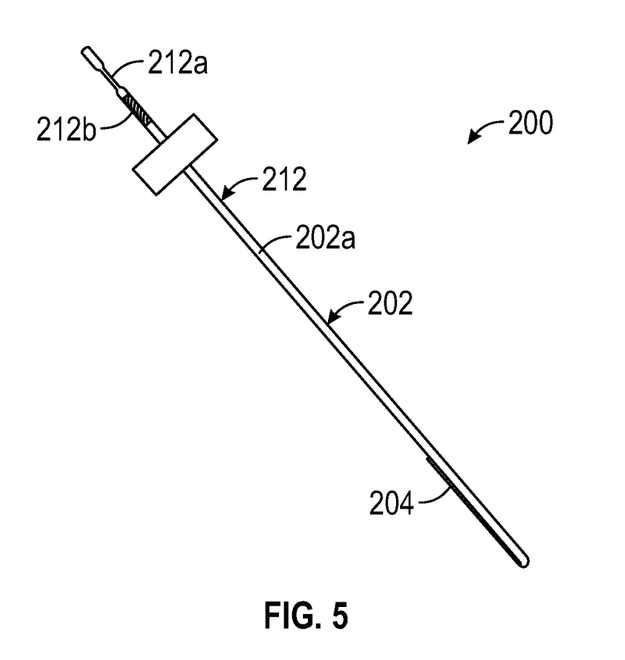
FIG. 5 is another side view of the ophthalmic surgical instrument of FIG. 4.

FIGS. 4 and 5 illustrate another embodiment of an ophthalmic surgical instrument, such as, for example, a capsular retractor 200, similar to the ophthalmic surgical instrument 100 described above. The capsular retractor 200 includes an elongated shaft 202, a hook portion 204 attached to a distal end portion 202b of the elongated shaft 202, and an elongated handle portion 212 attached to and angled from a proximal end portion 202a of the elongated shaft 202. The elongated handle portion 212 may be cylindrical along its length with a pair of first and second grasping segments 212a, 212b, such as, for example, flattened sections, formed in the elongated handle portion 212. The grasping segments 212a, 212b may be spaced longitudinally from one another along the length of the elongated handle portion 212. The grasping segments 212a, 21b are oriented perpendicular to one another so that a forceps may be used to grasp the elongated handle portion 212 when the elongated handle portion 212 is oriented in various rotational positions. The flattened sections 212a, 212b may be formed by heating and applying a compressive pressure to the sections 212a, 212b of the elongated handle portion 212.

Figure 6:
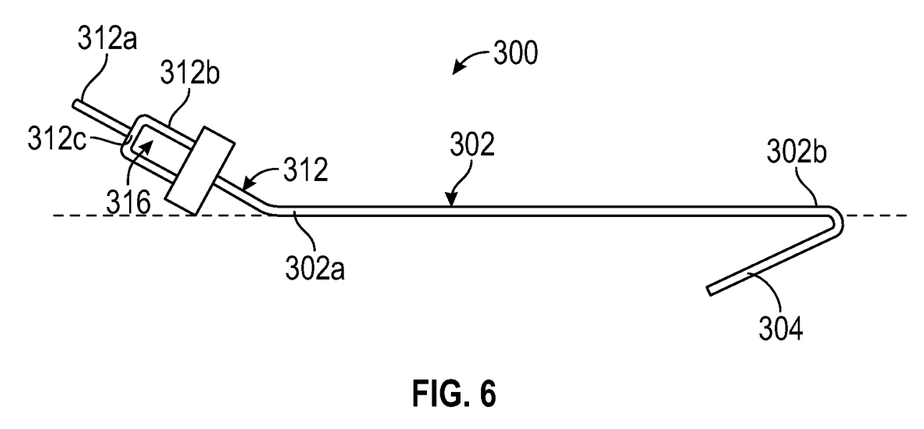
FIG. 6 is a side view of yet another embodiment of an ophthalmic surgical instrument.
Figure 7:
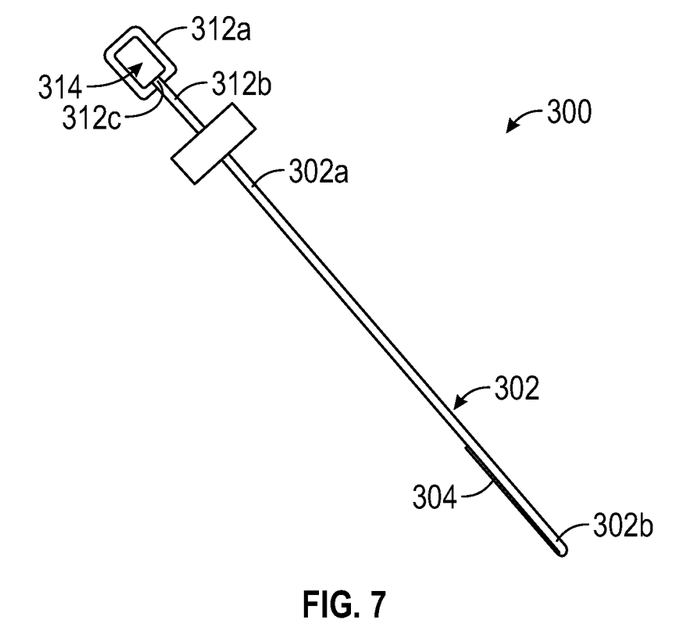
FIG. 7 is another side view of the ophthalmic surgical instrument of FIG. 6.

FIGS. 6 and 7 illustrate another embodiment of an ophthalmic surgical instrument, such as, for example, a capsular retractor 300, similar to the ophthalmic surgical instrument 100 described above. The capsular retractor 300 includes an elongated shaft 302, a hook portion 304 attached to a distal end portion 302b of the elongated shaft 302, and an elongated handle portion 312 attached to and angled from a proximal end portion 302a of the elongated shaft 302. The elongated handle portion 312 may be an elongated loop formed from a wire or a rod. The elongated handle portion 312 has a proximal end portion 312a and a distal end portion 312b that is offset (e.g., perpendicular) relative to the proximal end portion 312a. The proximal and distal end portions 312a, 312b may be formed by twisting the elongated loop 312 about a central region 312c between the proximal end distal end portions 312a, 312b, such that central openings 314, 316 defined through the respective proximal and distal end portions 312a, 312b are perpendicular to one another.

Figure 8:
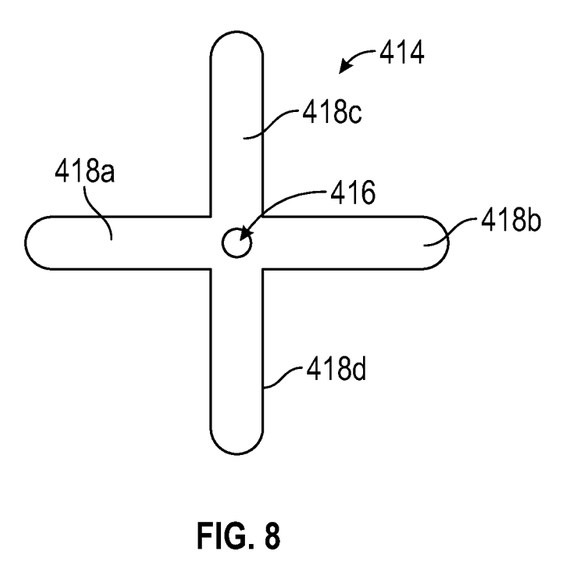
FIG. 8 is a top view of a stopper for use with any of the embodiments of the disclosed ophthalmic surgical instruments.
Figure 9:
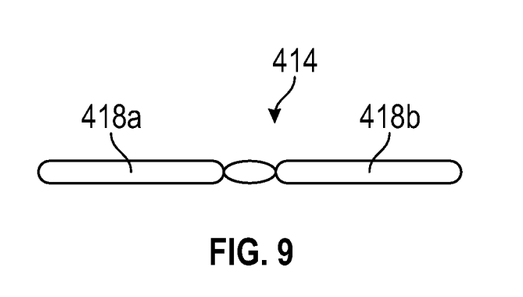
FIG. 9 is a side view of the stopper of FIG. 8.

FIGS. 8 and 9 illustrate another embodiment of a stopper 414 for use with any of the ophthalmic surgical instruments 100, 200, or 300 described herein. The stopper 414 defines a central passageway 416 for receipt of the elongated handle portion 112, 212, or 312, such that the stopper 414 is axially slidable along the elongated handle portion. The stopper 414 has a substantially flat transverse cross-sectional configuration (FIG. 9) and includes a plurality (e.g., four), struts or arms 418a, 418b, 418c, 418d extending radially outward from the central passageway 416. The struts 418a, 418b, 418c, 418d may together form a plus sign configuration. The struts 416 assist a clinician in grasping the stopper 414 for manipulation of the ophthalmic surgical instrument.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An ophthalmic surgical instrument for stabilizing a lens capsule, comprising:
   an elongated shaft having a proximal end portion and a distal end portion;
   a hook portion extending from the distal end portion of the elongated shaft;
   a handle portion extending from the proximal end portion of the elongated shaft;
   a first arm extending laterally from and being monolithically formed with the handle portion; and
   a second arm extending laterally from and being monolithically formed with the handle portion and longitudinally spaced along the elongated shaft from the first arm, the first and second arms oriented at a non-parallel angle relative to one another, wherein the first and second arms are configured to be selectively grasped for manipulating the ophthalmic surgical instrument, and wherein the first and second arms each extend laterally the same distance from the handle portion as one another.

2. The ophthalmic surgical instrument according to claim 1, wherein the angle between the first and second arms is from about 10 degrees to about 90 degrees.

3. The ophthalmic surgical instrument according to claim 1, wherein the first and second arms are perpendicular to one another and a longitudinal axis defined by the handle portion.

4. The ophthalmic surgical instrument according to claim 1, wherein the first arm has a first end portion projecting from a first side of the handle portion, and a second end portion projecting from a second side of the handle portion.

5. The ophthalmic surgical instrument according to claim 4, wherein the second arm has a first end portion projecting from a third side of the handle portion, and a second end portion projecting from a fourth side of the handle portion.

6. The ophthalmic surgical instrument according to claim 5, wherein the first and second sides of the handle portion oppose one another, and the third and fourth sides of the handle portion oppose one another.

7. The ophthalmic surgical instrument according to claim 1, wherein the hook portion extends at an acute angle relative to a longitudinal axis defined by the elongated shaft.

8. The ophthalmic surgical instrument according to claim 7, wherein the handle portion extends at an obtuse angle relative to the longitudinal axis of the elongated shaft.

9. The ophthalmic surgical instrument according to claim 7, wherein the elongated shaft defines:
   a first longitudinally-extending plane; and
   a second longitudinally-extending plane, perpendicular to the first plane, the hook portion and the handle portion being coplanar with the first plane, and the hook portion and the handle portion being disposed on opposite sides of the second plane.

10. The ophthalmic surgical instrument according to claim 1, wherein each of the first and second arms has a flat, rectangular shape.

11. The ophthalmic surgical instrument according to claim 1, further comprising a stopper disposed about the handle portion at a location distally of the first and second arms.

12. An ophthalmic surgical instrument for stabilizing a lens capsule, comprising:
    an elongated shaft defining a longitudinal axis and having a proximal end portion and a distal end portion;
    a hook portion extending at an acute angle relative to the distal end portion of the elongated shaft; and
    a handle assembly attached to the proximal end portion of the elongated shaft and including:
        an elongated handle portion;
        a first arm extending outwardly from opposite first and second sides of the elongated handle portion; and
        a second arm extending outwardly from opposite third and fourth sides of the elongated handle portion, wherein the first and second arms are configured to be selectively grasped for manipulating the ophthalmic surgical instrument, and wherein the first and second arms each extend outwardly the same distance from the elongated handle portion as one another.

13. The ophthalmic surgical instrument according to claim 12, wherein the first and second arms are oriented at a non-parallel angle relative to one another.

14. The ophthalmic surgical instrument according to claim 13, wherein the angle between the first and second arms is from about 45 degrees to about 90 degrees.

15. The ophthalmic surgical instrument according to claim 12, wherein the first and second arms are perpendicular to one another and the longitudinal axis of the elongated handle portion.

16. The ophthalmic surgical instrument according to claim 12, wherein the elongated shaft defines:
    a first longitudinally-extending plane; and
    a second longitudinally-extending plane, perpendicular to the first plane, the hook portion and the elongated handle portion being coplanar with the first plane, and the hook portion and the elongated handle portion being disposed on opposite sides of the second plane.

17. The ophthalmic surgical instrument according to claim 12, wherein each of the first and second arms has a flat, rectangular shape.

18. A capsular retractor, comprising:
    an elongated shaft having a proximal end portion and a distal end portion;
    a hook portion extending from the distal end portion of the elongated shaft; and
    an elongated handle portion attached to the distal end portion of the elongated shaft and including:

a first depression formed in the elongated handle portion; and a second depression formed in the elongated handle portion and disposed perpendicular to the first depression, wherein the first and second depressions are configured to be selectively grasped for manipulating the ophthalmic surgical instrument.

19. The ophthalmic surgical instrument according to claim 18, wherein the second depression is disposed distally of the first depression.

20. The ophthalmic surgical instrument according to claim 18, wherein each of the first and second depressions is flat relative to a remainder of the elongated handle portion and defines a plane, the plane of the first depression being perpendicular to the plane of the second depression, and wherein the first and second depressions extend longitudinally along a longitudinal axis defined by the elongated handle portion.

* * * * *

UNITED STATES PATENT AND TRADEMARK OFFICE
CERTIFICATE OF CORRECTION

| | | |
|---|---|---|
| PATENT NO. | : 10,639,195 B1 | Page 1 of 1 |
| APPLICATION NO. | : 16/544300 | |
| DATED | : May 5, 2020 | |
| INVENTOR(S) | : Richard Mackool | |

It is certified that error appears in the above-identified patent and that said Letters Patent is hereby corrected as shown below:

In the Claims

Claim 18, Column 8, Line 66, delete the word "distal" and insert the word --proximal--

Signed and Sealed this
Twenty-third Day of June, 2020

Andrei Iancu
*Director of the United States Patent and Trademark Office*